United States Patent
Matsumura et al.

(10) Patent No.: US 11,998,274 B2
(45) Date of Patent: Jun. 4, 2024

(54) OPHTHALMIC PHOTOGRAPHING APPARATUS (71) Applicant: Kowa Company, Ltd., Aichi (JP)

(72) Inventors: Kazunori Matsumura, Tokyo (JP); Akio Kawakami, Tokyo (JP)

(73) Assignee: Kowa Company, Ltd., Aichi (JP)

( * ) Notice: Subject to any disclaimer, the term of this patent is extended or adjusted under 35 U.S.C. 154(b) by 589 days.

(21) Appl. No.: 17/266,973

(22) PCT Filed: Aug. 7, 2019

(86) PCT No.: PCT/JP2019/031186
§ 371 (c)(1),
(2) Date: Feb. 8, 2021

(87) PCT Pub. No.: WO2020/032128
PCT Pub. Date: Feb. 13, 2020

(65) Prior Publication Data
US 2021/0307604 A1 Oct. 7, 2021

(30) Foreign Application Priority Data
Aug. 8, 2018 (JP) .................... 2018-149401

(51) Int. Cl.
*A61B 3/11* (2006.01)
*A61B 3/00* (2006.01)
*A61B 3/15* (2006.01)

(52) U.S. Cl.
CPC ............ *A61B 3/112* (2013.01); *A61B 3/0008* (2013.01); *A61B 3/15* (2013.01)

(58) Field of Classification Search
CPC ......... A61B 3/112; A61B 3/0008; A61B 3/15; A61B 3/12; A61B 3/14; A61B 3/152
(Continued)

(56) References Cited

U.S. PATENT DOCUMENTS
2014/0132924 A1   5/2014  Sagano

FOREIGN PATENT DOCUMENTS
DE   102016104417 A1   9/2017
EP       2138093 A1   12/2009
(Continued)

OTHER PUBLICATIONS

Extended European Search Report, issued in Application No. 19848180.6, dated Mar. 17, 2022.
(Continued)

*Primary Examiner* — Mohammed A Hasan
(74) *Attorney, Agent, or Firm* — Knobbe, Martens, Olson & Bear, LLP (57) ABSTRACT

An ophthalmic photographing apparatus enables easy detection of a pupil diameter. The ophthalmic photographing apparatus is provided with an anterior ocular segment illumination unit for illuminating an anterior ocular segment of a subject eye with invisible light, an imaging element that is sensitive to at least invisible light and captures an image of the subject eye, and a processing unit for processing the image captured by the imaging element. When an image of an index projected onto the anterior ocular segment satisfies a predetermined condition, the processing unit starts detection of a pupil diameter of the subject eye by using the image on the imaging element formed by invisible light reflected from the anterior ocular segment.

4 Claims, 9 Drawing Sheets (58) Field of Classification Search
USPC .......................................................... 351/204
See application file for complete search history.

(56) References Cited

FOREIGN PATENT DOCUMENTS

| | | | | | |
|---|---|---|---|---|---|
| EP | 3834708 | A1 | * | 6/2021 | ........... A61B 3/0008 |
| JP | 2001017394 | A | | 1/2001 | |
| JP | 2003290145 | A | | 10/2003 | |
| JP | 2010136781 | A | | 6/2010 | |
| JP | 4838459 | B2 | * | 12/2011 | |
| JP | 2014094182 | A | | 5/2014 | |
| JP | 5511575 | B2 | | 6/2014 | |
| JP | 5784056 | B2 | | 9/2015 | |
| JP | 2016055123 | A | * | 4/2016 | |
| JP | 2016055123 | A | | 4/2016 | |
| JP | 2016067766 | A | * | 5/2016 | |

OTHER PUBLICATIONS

International Search Report of PCT/JP2019/031186, dated Oct. 29, 2019.
Office Action issued in Chinese Application No. 201980052200.2, dated Mar. 5, 2024.

* cited by examiner

OPHTHALMIC PHOTOGRAPHING APPARATUS

FIELD

The present invention relates to an ophthalmic photographing apparatus.

BACKGROUND

When an ocular fundus is observed or photographed, the relative positional adjustment between a camera and a subject eye (e.g., see PTL 1), and various operations in accordance with the pupil diameter (e.g., see PTL 2 to PTL 5) are performed.

CITATION LIST

Patent Literature

[PTL 1] Japanese Patent Application Publication No. 2001-17394
[PTL 2] Japanese Patent Application Publication No. 2010-136781
[PTL 3] Japanese Patent Application Publication No. 2003-290145
[PTL 4] Japanese Patent No. 5511575
[PTL 5] Japanese Patent No. 5784056

SUMMARY

Technical Problem

Observing and photographing an ocular fundus are influenced by the size of a pupil. Therefore, when an ocular fundus is observed or photographed, an apparatus is adjusted in accordance with the size of the pupil before observing or photographing the ocular fundus, for example, so as to acquire accurate ocular fundus images. However, the relative positional relationship between a camera and the subject eye and the pupil diameter are easily changed by various factors, hence it is not easy to detect a pupil diameter accurately before observing or photographing the ocular fundus.

With the foregoing in view, the present application discloses an ophthalmic photographing apparatus that can easily detect a pupil diameter.

Solution to Problem

To solve the above problem, according to the present invention, when an image of an index projected onto an anterior ocular segment satisfies a predetermined condition, detection of a pupil diameter of a subject eye is started using an image that is formed on an imaging element by reflected light of invisible light from an anterior ocular segment.

Specifically, the present invention is an ophthalmic photographing apparatus including: an anterior ocular segment illumination unit for illuminating an anterior ocular segment of a subject eye with invisible light; an imaging element that is sensitive to at least invisible light and that captures the image of a subject eye; and a processing unit for processing the image captured by the imaging element. When an image of an index projected onto the anterior ocular segment satisfies a predetermined condition, the processing unit starts detection of a pupil diameter of the subject eye by using the image on the imaging element formed by reflected light from the anterior ocular segment, which is reflected light of invisible light emitted from the anterior ocular segment illumination unit.

Here, the anterior ocular segment refers to a front side portion of an eyeball, and is a portion from a cornea to a crystalline lens, for example. The invisible light refers to light that is not perceived by human eyes, and may be infrared light, for example. The predetermined condition refers to a state of an image of an index that is projected onto the anterior ocular segment in a case where the subject eye is at a proper position, and, for example, may be a state where an index that indicates a distance between an object lens of the ophthalmic photographing apparatus and the subject eye signifies that the subject eye is at a proper position.

With this ophthalmic photographing apparatus, the detection of the pupil diameter is started when the image of the index projected onto the anterior ocular segment satisfies a predetermined condition, and the pupil diameter can be easily detected. As a result, the observer can smoothly acquire an ocular fundus image of the subject by a simple operation.

The processing unit may, when detecting that an image of an index for distance measurement projected onto the anterior ocular segment is at a predetermined position within the image formed on the imaging element, start detection of the pupil diameter by using the image on the imaging element formed by reflected light from the anterior ocular segment, which is reflected light of invisible light emitted from the anterior ocular segment illumination unit. Here, the predetermined position refers to a position of the index projected onto the anterior ocular segment in a case where the subject eye is at a proper position, and, for example, may be a position within the image in a case where the index that indicates a distance between the objective lens of the ophthalmic photographing apparatus and the subject eye signifies that the subject eye is at a proper position. With this ophthalmic photographing apparatus, the detection of the pupil diameter is started when the distance between the objective lens of the ophthalmic photographing apparatus and the subject eye becomes a proper distance, and the pupil diameter can be easily detected.

The ophthalmic photographing apparatus may further include switching unit for switching a region to be imaged on the imaging element between the ocular fundus of the subject eye and the anterior ocular segment, and the processing unit may, upon completion of the detection of the pupil diameter, use the switching unit to switch the region to be imaged on the imaging element from the anterior ocular segment to the ocular fundus. With this ophthalmic photographing apparatus, an image formed on the imaging element changes from an image of the anterior ocular segment to an image of the ocular fundus immediately after detection of the pupil diameter completes, and the observer can smoothly acquire the ocular fundus image of the subject by a simple operation.

The processing unit may also scan luminous values along a virtual line, which intersects with at least a boundary between an iris and a pupil of the subject eye, within the image, and detect the pupil diameter from a position of a boundary point between the iris and the pupil of the subject eye extracted based on a change amount of the luminance value. With this ophthalmic photographing apparatus, load of arithmetic processing relating to the detection of the pupil diameter can be reduced.

The processing unit may also scan the luminance values along a plurality of the virtual lines, and detect the pupil diameter from positions of a plurality of the boundary points. With this ophthalmic photographing apparatus, both suppression of detection errors of the pupil diameter and reduction of loads of arithmetic processing can be implemented.

Advantageous Effects of Invention

With the ophthalmic photographing apparatus above, the pupil diameter can be easily detected.

DETAILED DESCRIPTION OF THE PREFERRED EMBODIMENT

An embodiment of the present invention will now be described. The following embodiment is an example of the embodiments of the present invention, and is not intended to limit the technical scope of the present invention.

Figure 1:
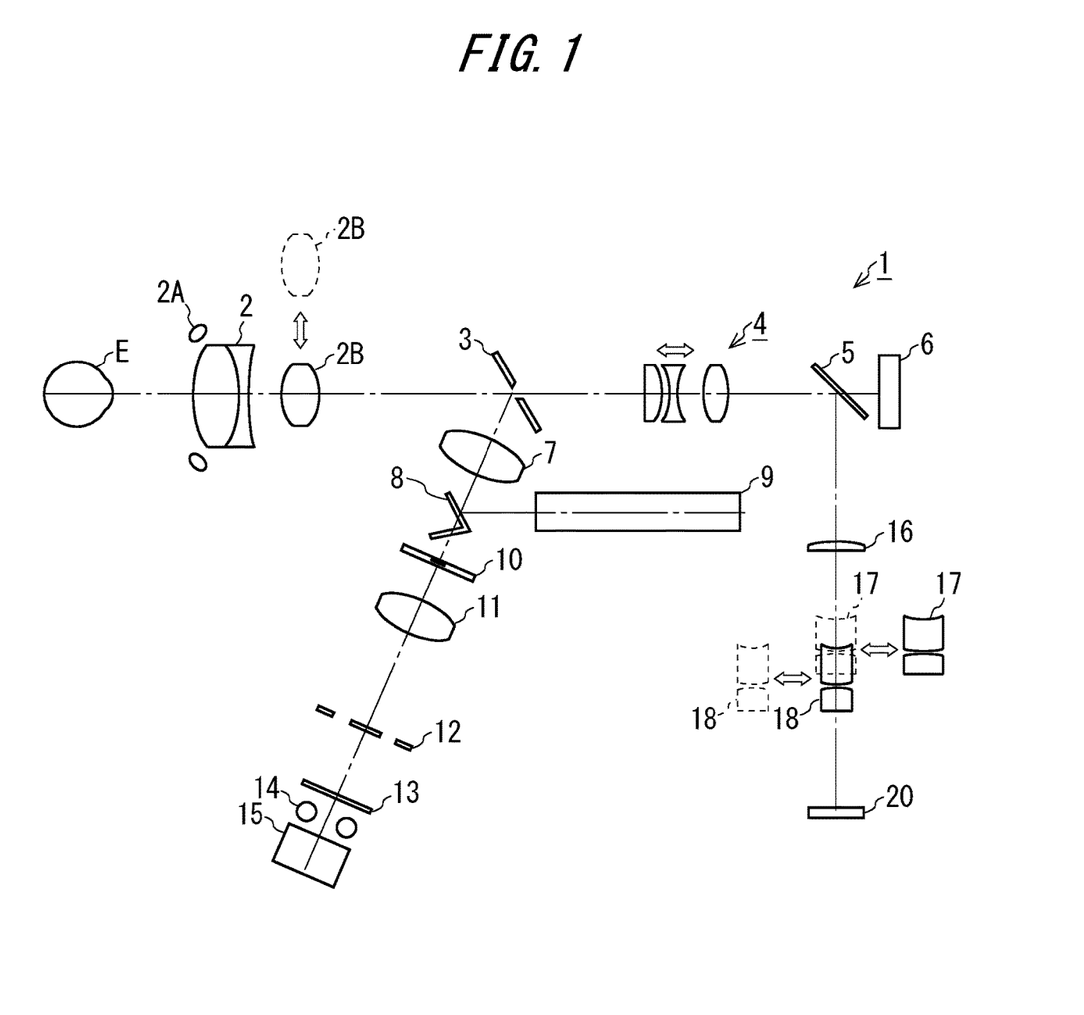
FIG. 1 is a diagram depicting a general configuration of an optical system of an ophthalmic photographing apparatus according to an embodiment.

FIG. 1 is a diagram depicting a general configuration of an optical system of an ophthalmic photographing apparatus of the present embodiment. The ophthalmic photographing apparatus 1 is an apparatus that photographs an ocular fundus of a subject eye E, and includes: an objective lens 2, an anterior ocular segment illumination 2A (an example of the "anterior ocular segment illumination unit" of the present application), an anterior ocular segment imaging lens 2B; a perforated mirror 3, a focus lens 4, a half mirror 5, an internal fixation lamp 6, a relay lens 7, a focus dot mirror 8, a focus index projection system 9, a black spot plate glass 10, a relay lens 11, a ring slit 12, a diffusion plate 13, an illumination for photographing 14, an illumination for observation 15, an imaging lens 16, a narrow angle lens 17, a wide angle lens 18, and an image sensor 20 (an example of the "imaging element" of the present application).

First a positional relationship of each component included in the ophthalmic photographic apparatus 1 and each function thereof will be described. The objective lens 2 is a lens located in front of the subject eye E. The anterior ocular segment illumination 2A is an infrared light emitting diode (LED) which has both a function to illuminate the anterior ocular segment of the subject eye E with the infrared light, and a function to project an index for distance measurement onto the anterior ocular segment of the subject eye E. On the optical axis behind the objective lens 2, the anterior ocular segment imaging lens 2B, the perforated mirror 3, the focus lens 4, the half mirror 5 and the internal fixation lamp 6 are disposed sequentially. The anterior ocular segment imaging lens 2B is a movable lens that is inserted into/withdrawn from the optical axis behind the objective lens 2, and is moved by an actuator (an example of the "switching unit" of the present application) interlocking with a switching button (hereafter referred to as the "anterior ocular segment/ocular fundus switching button") disposed in the ophthalmic photographing apparatus 1, and a control signal. The perforated mirror 3 is a mirror where a through hole is formed at a region where the optical axis of the objective lens 2 passes through, and is fixed inside the ophthalmic photographing apparatus 1 at an appropriate tilt angle with respect to the optical axis of the objective lens 2.

On the illumination optical system that guides the illumination light, which is reflected by the perforated mirror 3 and is emitted to the subject eye E, the relay lens 7, the focus dot mirror 8, the black spot plate glass 10, the relay lens 11, the ring slit 12, the diffusion plate 13, the illustration for photographing 14 and the illumination for observation 15 are disposed in sequence from the perforated mirror 3 side. Therefore each light emitted from the illumination for photographing 14 and the illumination for observation 15 becomes an annular illumination light while passing through the diffusion plate 13 and the ring slit 12, propagates through the relay lens 11, the black spot plate glass 10, the focus dot mirror 8 and the relay lens 7, and is then reflected by the perforated mirror 3, whereby the ocular fundus of the subject eye E is illuminated via the objective lens 2.

The black spot plate glass 10 prevents the light reflected by the objective lens 2 from being captured in the photographed image, and includes a small light-shielding substance which is disposed at the center of the plate glass, that is, at a position where the optical axis passes through. The light from the focus index projection system 9 enters the focus dot mirror 8, which is disposed between this black spot plate glass 10 and the relay lens 7, at an angle matching with the optical axis of the relay lens 7. The focus index projection system 9 projects a focus index onto the ocular fundus of the subject eye E. This unit that not only the light emitted by the illumination for photographing 14 and the illumination for observation 15, but also the light of the focus index emitted by the focus index projection system 9 enters the ocular fundus of the subject eye E. A red LED which emits infrared light is used for the focus index projection system 9.

The light reflected by the ocular fundus of the subject eye E, illuminated with the illumination for photographing 14 and the illumination for observation 15, passes through the objective lens 2, the perforated mirror 3 and the focus lens 4, and enters the half mirror 5. The half mirror 5 is fixed inside the ophthalmic photographing apparatus 1 at an appropriate tilt angle with respect to the optical axis of the objective lens 2. Therefore the light reflected by the ocular fundus of the subject eye E is reflected by the half mirror 5 at an appropriate angle with respect to the optical axis of the objective lens 2. On the optical axis of the light, which entered from the focus lens 4 and was reflected by the half mirror 5, the imaging lens 16 and the image sensor 20 are disposed in sequence. Between the imaging lens 16 and the image sensor 20, a narrow angle lens 17 or a wide angle lens 18, which is a variable power lens that is properly selected in accordance with the magnification desired by the observer, is inserted. The light reflected by the ocular fundus of the subject eye E is reflected by the half mirror 5 and passes through the imaging lens 16, then enters the image sensor 20 via the narrow angle lens 17 or the wide angle lens 18. In the image sensor 20, photoelectric conversion elements, which are arrayed in a matrix, receive the energy of the light and emit electric signals, whereby an image of the ocular fundus of the subject eye E is acquired.

The image sensor 20 is an imaging element that is sensitive to at least visible light and infrared light. Therefore the image sensor 20 can acquire an image of the anterior ocular segment or the ocular fundus regardless whether the light source of the light emitted to the subject eye E is the anterior ocular segment illumination 2A with which the anterior ocular segment of the subject eye E is illuminated, the illumination for photographing 14 with which the ocular fundus of the subject eye E is illuminated, and the illumination for observation 15 with which the ocular fundus of the subject eye E is illuminated. An example of this kind of image sensor 20 is CMOS.

In the ophthalmic photographing apparatus 1, a photographing apparatus main body, which includes the above mentioned optical system components in a housing, is mounted on a frame. Further, the ophthalmic photographing apparatus 1 includes a moving mechanism that moves the housing mounted on the frame in the front/back, left/right and up/down directions by operating an operation lever, so that the positional relationship of the photographing apparatus main body with respect to the subject eye E can be adjusted by operating the operation lever.

Figure 2:
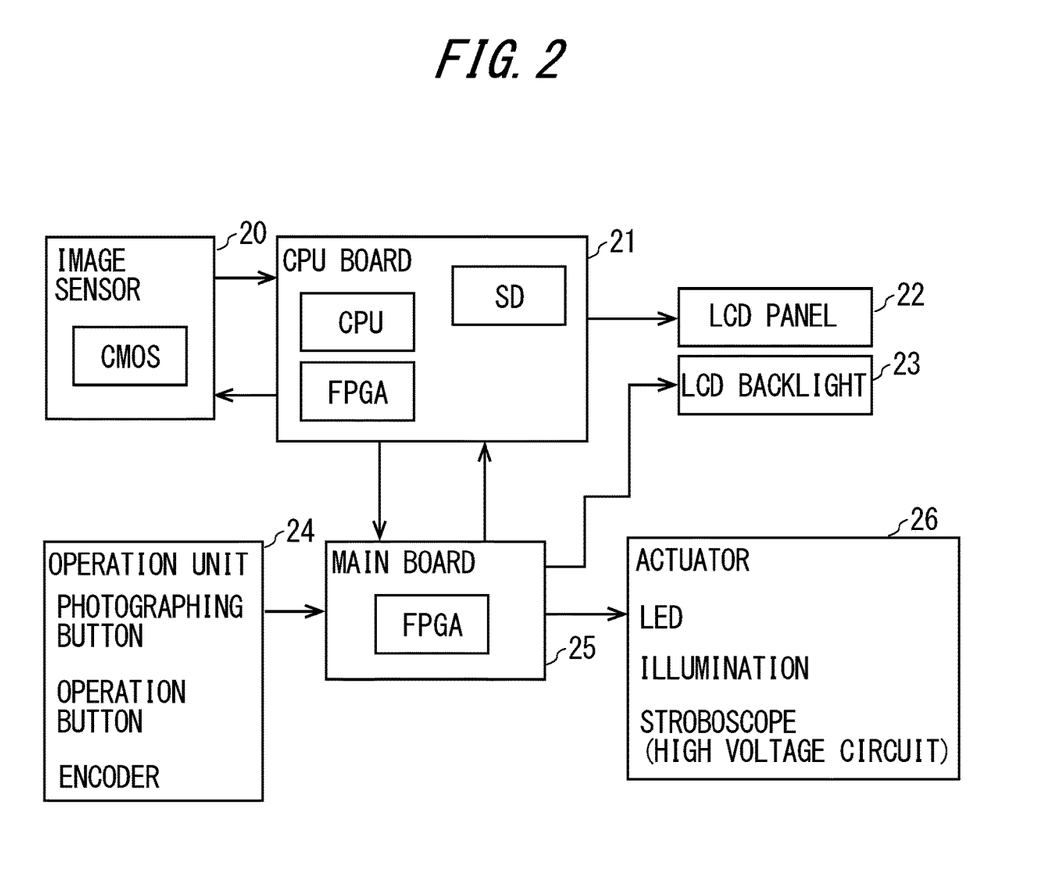
FIG. 2 is an example of a block diagram of an electric circuit included in the ophthalmic photographing apparatus.

FIG. 2 is an example of a block diagram of an electric circuit (an example of the "processing unit" of the present application) included in the ophthalmic photographing apparatus 1. The ophthalmic photographing apparatus 1 includes, for example, a CPU board 21, a liquid crystal display (LCD) panel 22, an LCD backlight 23, an operation unit 24, and a main board 25. In FIG. 2, an actuator that moves the focus lens 4, a high voltage circuit that causes the illumination for photographing 14 to emit light, an LED included in the focus index projection system 9 and the illumination for observation 15 are all included in the electronic components 26.

The CPU board 21 is a circuit board that mainly plays a role of processing images acquired by the image sensor 20, and on the CPU board 21, various electronic components, such as a central processing unit (CPU) that processes images, a field programmable gate array (FPGA), and a drive for an SD card ("SD" is a registered trademark) that records images, are mounted. The image sensor 20 operates in accordance with a control signal of the CPU board 21, and provides the acquired image to the CPU board 21. In the CPU board 21, various processing steps are executed on the image acquired by the image sensor 20, and the processed image is outputted to the LCD panel 22 or the SD card. On the LCD panel 22, the image outputted from the CPU board 21 is displayed.

The main board 25 is a circuit board that controls the ophthalmic photographing apparatus 1 in general, and on the main board 25, FPGA and various other electronic components are mounted. The main board 25 operates the CPU board 21 and the electronic components 26 in accordance with the operation content received by the operation unit 24. The main board 25 implements the following processing flow.

Figure 3:
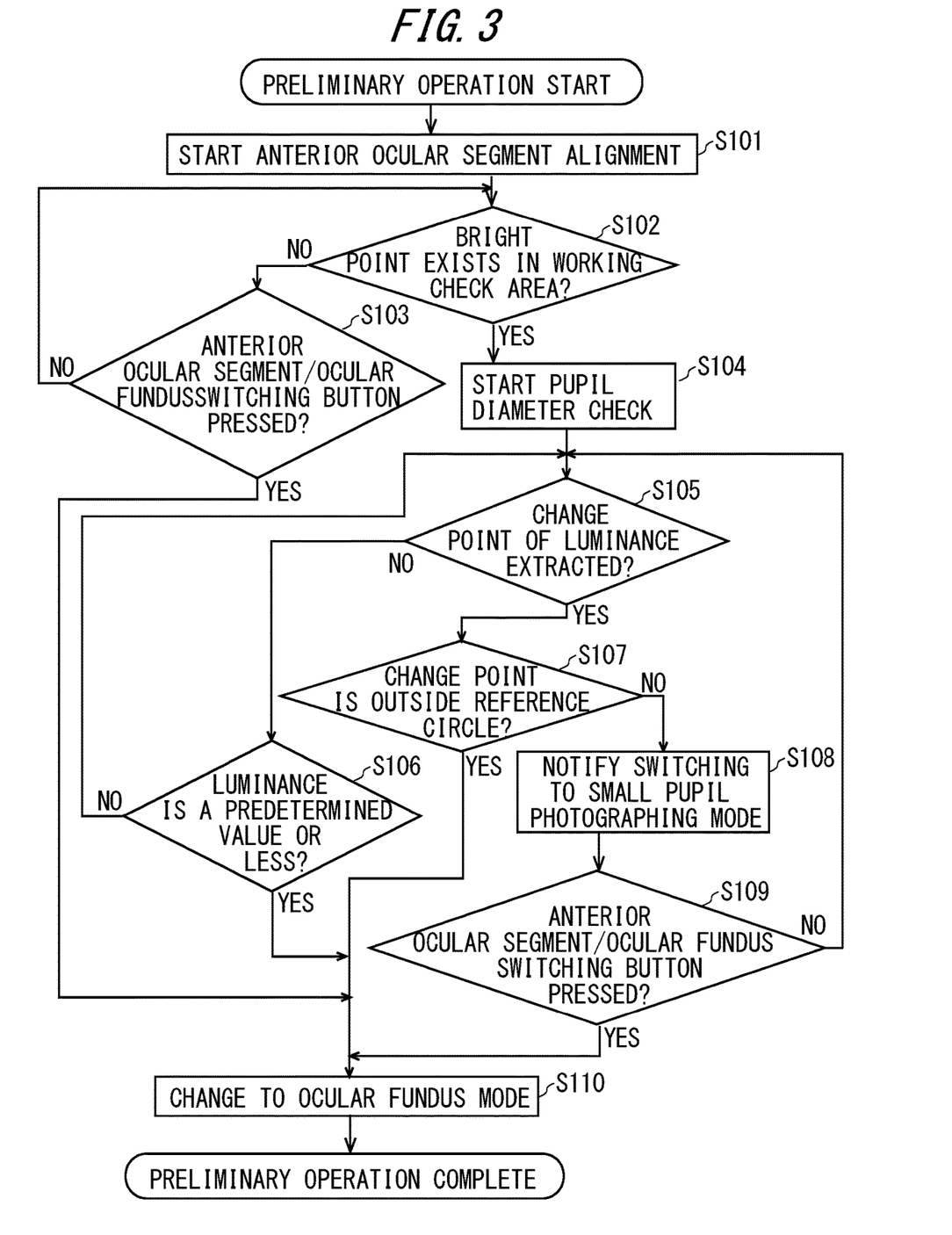
FIG. 3 is a flow chart depicting a processing flow implemented by the ophthalmic photographing apparatus.

FIG. 3 is a flow chart depicting processing flow implemented by the ophthalmic photographing apparatus 1. When the ophthalmic photographing apparatus 1 is started, the image sensor 20 is activated, and power is supplied to the illumination for observation 15. At the start of the ophthalmic photographing apparatus 1, the anterior ocular segment mode, in which the anterior ocular segment of the subject eye E is displayed on the LCD panel 22, is selected, hence in this state, the anterior ocular segment imaging lens 2B is inserted on the optical axis, and power is also supplied to the anterior ocular segment illumination 2A, with which the anterior ocular segment is illuminated. Then in the ophthalmic photographing apparatus 1, alignment adjustment is performed so that the anterior ocular segment of the subject eye E is clearly displayed (S101).

Figure 4:
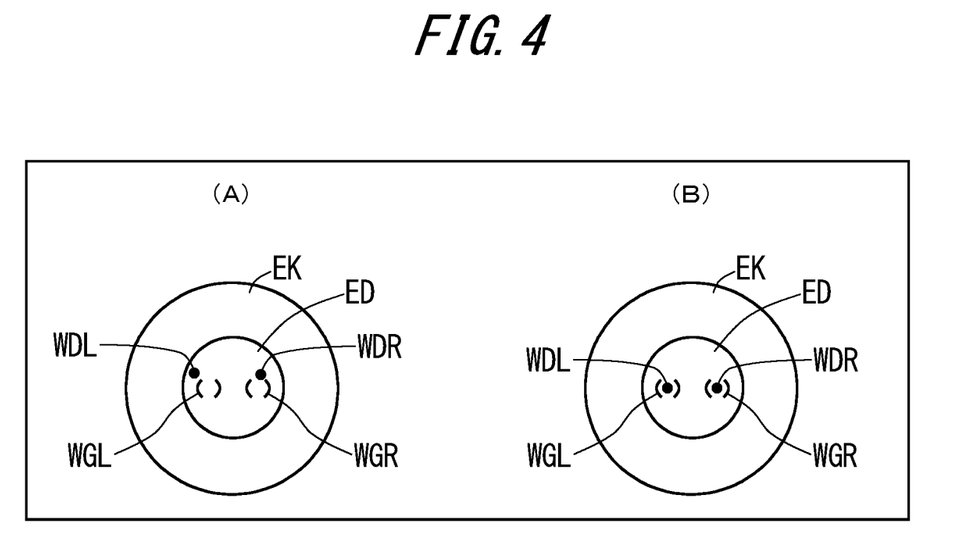
FIG. 4 is a diagram depicting an example of images displayed on an LCD panel when alignment of an anterior ocular segment is adjusted.

Adjustment of the anterior ocular segment is adjusted as follows. FIG. 4 is a diagram depicting an example of images displayed on the LCD panel 22 when alignment of the anterior ocular segment is adjusted. FIG. 4(A) indicates a state where the anterior ocular segment is not aligned, and FIG. 4(B) indicates a state where the anterior ocular segment is aligned. Since the anterior ocular segment of the subject eye E is illuminated with the anterior ocular segment illumination 2A, indexes WDL and WDR are displayed on the LCD panel 22 of the ophthalmic photographing apparatus 1 by the cornea reflection of the light emitted from the anterior ocular segment illumination 2A. The indexes WDL and WDR are indexes for distance measurement, to indicate the distance between the subject eye E and the objective lens 2. While observing the LCD panel 22, the observer operates the operation lever so that the index WDL enters a working alignment guide WGL, and the index WDR enters a working alignment guide WGR. The working alignment guides WGL and WGR indicate the positions of the indexes WDL and WDR in the image (an example of the "predetermined position" of the present application) in the case where the subject eye E and the objective lens 2 have a proper distance. Therefore when the positional relationship of the photographing apparatus main body with respect to the subject eye E is adjusted, so that the index WDL enters the working alignment guide WGL and the index WDR enters the working alignment guide WGR, the positional relationship between the photographing apparatus main body and the subject eye E becomes a proper positional relationship that is specified in the design of the ophthalmic photographing apparatus 1.

While the alignment of the anterior ocular segment is adjusted, the main board 25 monitors an image that is in-process by the CPU board 21, and determines whether the index WDL entered the working alignment guide WGL and the index WDR entered the working alignment guide WGR (S102). While the determination result in the processing in step S102 is No, the main board 25 also determines whether the anterior ocular segment/ocular fundus switching button was pressed (S103). Then when the determination result in step S102 is Yes, the main board 25 starts checking the pupil diameter, which will be described below (S104).

Figure 5:
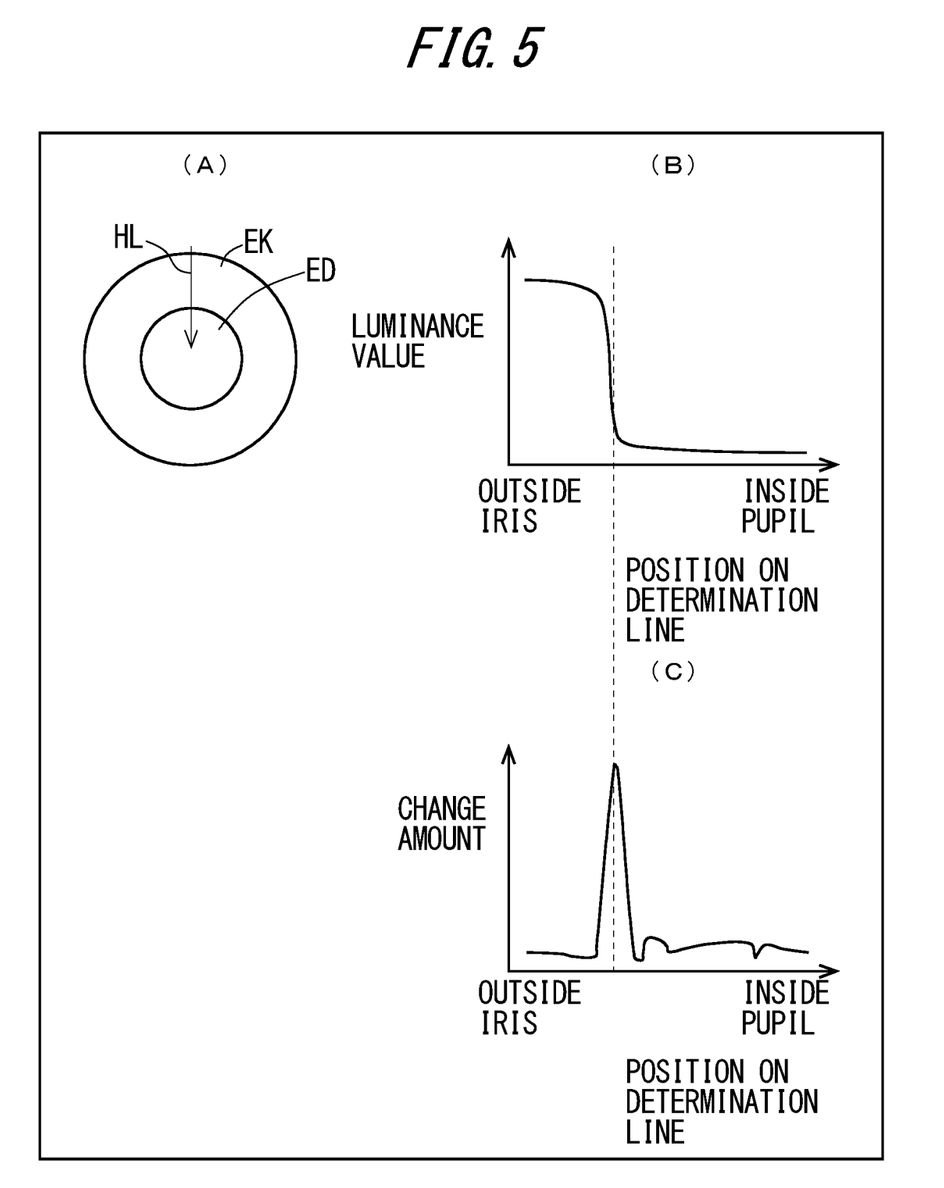
FIG. 5 is a first diagram for describing a structure to detect a pupil diameter.

FIG. 5 is a first diagram for describing a structure to detect a pupil diameter. Out of the light emitted to the anterior ocular segment of the subject eye E, the light that entered the iris EK is reflected by the iris EK, while the light that entered the pupil ED transmits through the pupil ED and enters the ocular fundus. Therefore in an image of the anterior ocular segment of the subject eye E, the luminance of pixels in a region where the region of the iris EK is projected is brighter than the luminance of pixels in a region where the region of the pupil ED is projected. Hence the main board 25 analyzes the luminance value of each pixel of the image that is processed by the CPU board 21, and detects the position of the boundary between the pupil ED and the iris EK. Here in order to reduce the load of the arithmetic processing related to the image analysis, the main board 25 does not extract the position of the boundary between the pupil ED and the iris EK continuously throughout the entire circumference of the annular boundary, but extracts the boundary position only at a plurality of discrete locations. In other words, in the main board 25, the processing to scan the luminance value of each pixel is performed along a line indicated by the reference sign HL (hereafter referred to as "determination line HL") in the image of the anterior ocular segment illustrated in FIG. 5(A), whereby the continuous data in the graph in FIG. 5(B) is acquired, and the place of the pixel where the luminous value changes most significantly in the continuous data is extracted as the boundary between the pupil ED and the iris EK.

The pixel at which the luminance value changes most significantly is determined by specifying a place which indicates the largest value in the data acquired by differentiating the continuous data of the brightness value of each pixel along the determination line HL, that is, the data indicated in the graph in FIG. 5(C). In the ophthalmic photographing apparatus 1 of the present embodiment, the boundary between the pupil ED and the iris EK is extracted not based on the luminous values but based on the change amount of the luminance values. An explanation of this reason follows. The pattern in the iris EK varies depending on the subject, the luminance value of the iris EK varies depending on the subject, therefore the boundary between the pupil ED and the iris EK may not be clearly indicated if this boundary is extracted based on the luminous values. On the other hand, the pupil ED is not a region where light is reflected, unlike the iris EK, hence the change of the luminance value becomes significant at the boundary between the pupil ED and the iris EK, and the boundary can be more clearly detected by extracting the boundary based on the change amount of the luminance values than by extracting the boundary based on the luminance values. However, the method of extracting the boundary between the pupil ED and the iris EK in the ophthalmic photographing apparatus 1 is not limited to the method of extracting the boundary based on the change amount of the luminance values, but may be a different method, including a method of extracting the boundary based on the luminance values.

Figure 6:
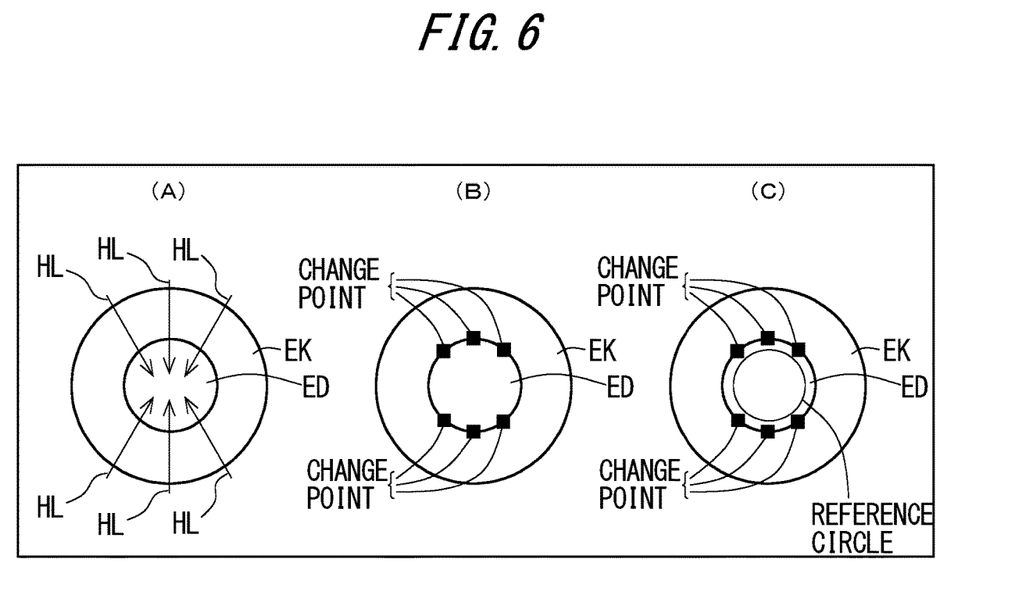
FIG. 6 is a second diagram for describing a structure to detect a pupil diameter.
Figure 7:
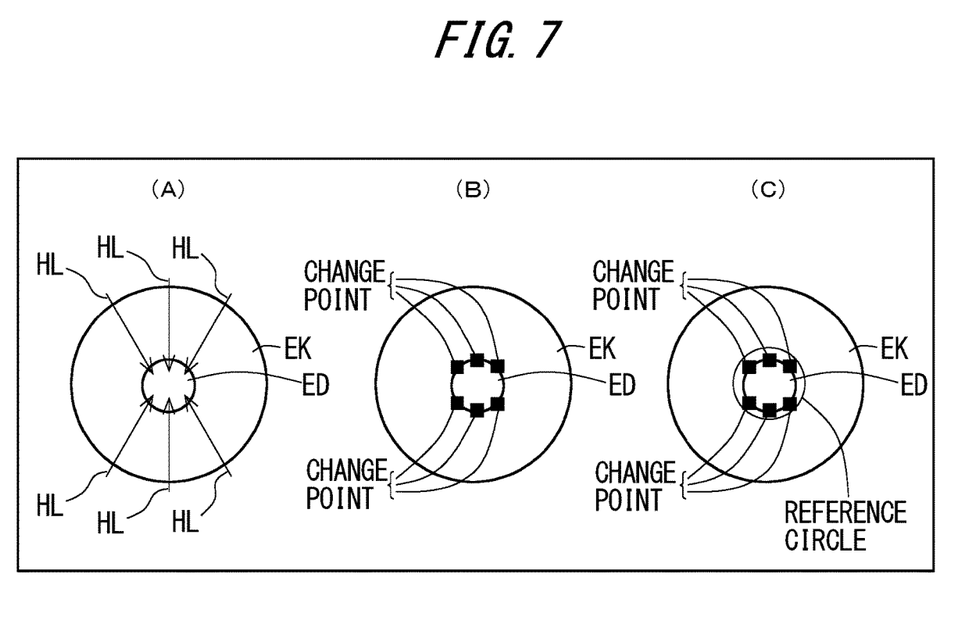
FIG. 7 is a third diagram for describing a structure to detect a pupil diameter.

FIG. 6 is a second diagram for describing a structure to detect a pupil diameter. Further, FIG. 7 is a third diagram for describing a structure to detect a pupil diameter. In order to extract the position of the boundary between the pupil ED and the iris EK at a plurality of discrete locations, the extraction of the position of the boundary between the pupil ED and the iris EK along the above mentioned determination line HL is performed in the main board 25, for each of a plurality of predetermined virtual determination lines HL respectively. In other words, in the main board 25, 6 determination lines HL, which are disposed so as to cross the boundary between the pupil ED and the iris EK at 6 locations, are set in advance, as illustrated in FIG. 6(A) and FIG. 7(A), and on each determination line HL, the change point at which the luminance changes is extracted as the boundary points. As a result, in the main board 25, the boundary points are extracted at 6 locations, as illustrated in FIG. 6(B) and FIG. 7(B). Boundary points at 6 locations are extracted in the present embodiment, but this determined considering only the balance between the suppression of detection errors of the pupil diameter and the load of the arithmetic processing, and the number of extraction locations of the boundary points is not limited to 6. For example, the ophthalmic photographing apparatus 1 may extract the boundary points at 5 or less locations, or at 7 or more locations. The luminance values may change largely due to accidently capturing an unintended image in an image, therefore if the pupil diameter is detected with fewer determination lines HL, a location that is not the boundary between the pupil ED and the iris EK may be extracted as a boundary point in error. Further, there is an individual difference in the shape of the pupil ED, therefore if the pupil diameter is detected with fewer determination lines HL, errors between the detected pupil diameter and the actual pupil diameter may increase in the case where the pupil ED has an elliptic shape. On the other hand, if the pupil diameter is detected with more determination lines HL, the volume of arithmetic processing increases, therefore time required for detecting the pupil diameter, for example, becomes longer.

In the main board 25, the boundary points are extracted like this, and then it is determined whether each extracted boundary point is located inside or outside a predetermined reference circle. The reference cycle is a circle of which diameter is the same as the diameter of a pupil when the ocular fundus of the subject eye E is imaged in the small pupil photographing mode in the ophthalmic photographing apparatus 1. In a case of a non-mydriatic fundus camera, it is preferable to select the small pupil photographing mode in order to prevent a decrease in the illumination light with which the occur fundus is illuminated. In this mode, in the case where the pupil diameter is not larger than the diameter of the reference circle, the inner diameter of the ring slit 12 is decreased or emission intensity of the illumination light is increased than in the case where the pupil diameter is larger than the diameter of the reference circle, so that a larger amount of annular illumination light enters the subject eye E, or the photographic aperture is changed. Therefore in the main board 25, it is determined whether the small pupil photographing mode is selected or not depending on whether each boundary point is located inside or outside the reference circle.

In other words, the main board 25 executes the processing in step S104 in FIG. 3, whereby the above mentioned processing to extract the boundary points along a determination line HL is performed for each of the 6 determination lines HL. Then the main board 25 executes the determination processing to determine whether the boundary points of the luminance values were extracted (S105), and executes the determination processing to determine whether each boundary point is located outside the reference circle (S107).

Further, in the case where the determination result in step S105 is No, the main board 25 determines whether the luminance values of the pixels along the determination line HL are a predetermined value or less (S106). The predetermined value here refers to a luminance value with which the pupil ED and the iris EK can be distinguished, and can be, for example, a median value between a mean value of luminance values of the pixels located in a place where the pupil ED is projected and a mean value of luminance values of the pixels located in a place where the iris EK is projected, or a median value between the maximum value of the luminance values of the pixels located in a place where the pupil ED is projected and a minimum value of the luminance values of the pixels located in a place where the iris EK is projected.

For example, in a case where the diameter of the pupil is larger than the diameter of the reference circle, as illustrated in FIG. 6(C), the boundary points are located outside the reference circle, hence the determination result in the processing in step S107 is Yes. In a case where the diameter of the pupil is smaller than the diameter of the reference circle, as illustrated in FIG. 7(C), the boundary points are located inside the reference circle, hence the determination result in the processing in step S107 is No. Further, for example, in a case where the diameter of the pupil is so large that each determination line HL is completely within the region of the pupil ED and the boundary points cannot be extracted along each determination line HL, the determination result in step S105 becomes No and the determination result in step S106 becomes Yes. Furthermore, for example, in a case where the diameter of the pupil is so small that each determination line HL is completely within the region of the iris EK and the boundary points cannot be extracted along each determination line HL, the determination results in step S105 and S106 become No respectively.

In the case where the determination result in the processing in step S107 is No, the main board 25 executes the processing to send a notification to the observer so as to switch the mode to the small pupil photographing mode (S108). Then the main board 25 determines whether the anterior ocular segment/ocular fundus switching button was pressed (S109). In the case where the determination result in the processing in any one of steps S103, S106, S107 and S109 is Yes, the main board 25 executes the processing to switch the state of each component of the ophthalmic photographing apparatus 1 from the anterior ocular segment mode, in which the anterior ocular segment of the subject eye E is projected onto the LCD panel 22, to the ocular fundus mode, in which the ocular fundus of the subject eye E is projected onto the LCD panel 22 (S110).

When each component of the ophthalmic photographing apparatus 1 is switched to the ocular fundus mode, the anterior ocular segment imaging lens 2B, which is inserted into the optical path, is withdrawn from the optical path. Then when the main board 25 activates the focus lens 4 and aligns the focal point to the ocular fundus, the image of the ocular fundus of the subject eye E is displayed on the LCD panel 22. Then, the ocular fundus is photographed by the observer pressing the shutter switch using the operation unit 24, for example.

As described above, in the ophthalmic photographing apparatus 1, the above mentioned automatic detection of the pupil diameter (S105 to S107) is executed in short timing after completion of the alignment adjustment of the anterior ocular segment (timing when the determination result in S102 became Yes), and before the anterior ocular segment imaging lens 2B is withdrawn from the optical path and the mode is automatically switched to the ocular fundus mode (timing before S110 is executed), therefore the pupil diameter can be easily detected compared with a case where the observer visually confirms the size of the pupil diameter after confirming the completion of the alignment adjustment of the anterior ocular segment, for example. Furthermore, in a case where the pupil ED, which temporarily shrinks once, continuously expands for any reason, even if the alignment adjustment of the anterior ocular segment completes, the processing steps are repeated in the sequence of steps S105, S107, S108, S109 and S105 in the ophthalmic photographing apparatus 1, so that the executions of the step S110 is suspended until the diameter of the pupil becomes larger than the diameter of the reference circle, unless the anterior ocular segment/ocular fundus switching button is pressed. Then, at the timing when the diameter of the pupil becomes larger than the diameter of the reference circle, the determination result in step S107 becomes Yes, and the processing in step S110 is executed, hence the switching of an image of the anterior ocular segment to an image of the ocular fundus can be automatically performed interlocking with the expansion of the pupil ED. As a result, the observer can acquire the image of the ocular fundus of the subject smoothly by a simple operation.

The illumination light with which the ocular fundus is illuminated can be changed by changing the inner diameter of the ring slit 12, changing the emission intensity of the illumination light, or changing the photographic aperture, for example, as mentioned above. More specifically, possible methods to change the illumination light are, for example: switching only the inner diameter of the ring slit when it is determined that the pupil diameter is relatively small; changing the diameter of the photographic aperture at the same time with switching the ring slit; increasing the emission quantity of the illumination for photographing 14; causing natural mydriasis by decreasing the light quantity of the internal fixation light 6; or increasing the emission quantity of the illumination for photographing 14 when it is determined that the pupil diameter is relatively small even after the time set by the observer elapsed. Further, in the case where it is determined that the pupil diameter is relatively small, and where the observer changed the anterior ocular segment mode to the ocular fundus mode without changing the state of the ophthalmic photographing apparatus 1 to the small pupil mode, even if the observer was notified by a notification unit that the pupil diameter is small via a screen display or the like, for example, the light quantity of the illumination light, with which the ocular fundus is illuminated, may be increased automatically. Furthermore, in the case where it is determined that the pupil diameter is relatively small, the communication unit included in the ophthalmic photographing apparatus 1 may decrease the illuminance around the ophthalmic photographing apparatus 1 by sending control signals to the light fixtures and control device for a dimming unit (e.g., blinds) disposed around the ophthalmic photographing apparatus 1, so that natural mydriasis of the subject eye E is caused.

While the ophthalmic photographing apparatus 1 has been described above, the ophthalmic photographing apparatus 1 is not limited to the above embodiment. For example, the ophthalmic photographing apparatus 1 may detect the boundary between the pupil ED and the iris EK by analyzing the entire region of the image acquired by the image sensor 20, instead of determining the pupil diameter by scanning the luminance values along the determination lines HL.

Figure 8:
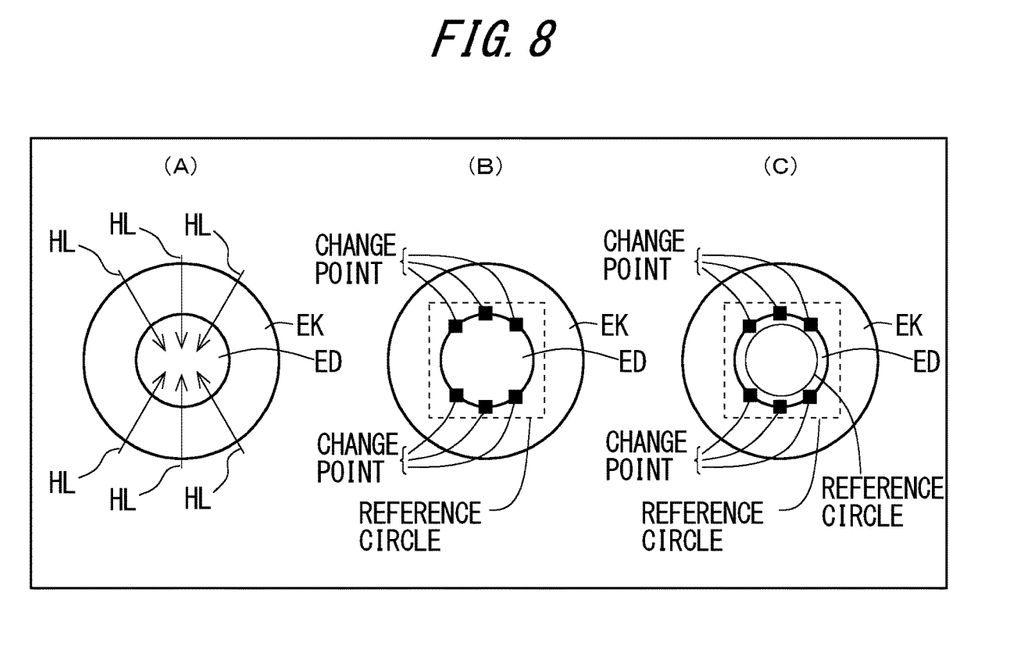
FIG. 8 is a diagram depicting an image of an extraction range of boundary points.

The ophthalmic photographing apparatus 1 may reduce the load of arithmetic processing related to the image analysis by limiting the range of the image where luminance values are scanned. FIG. 8 is a diagram depicting an image of an extraction range of boundary points. For example, the ophthalmic photographing apparatus 1 may perform the above mentioned boundary point extraction processing only for the portion within the broken line frame as the "processing range" in FIG. 8. By limiting the range of extracting the boundary points to a size in which an ordinary sized pupil ED appropriate to observe the ocular fundus is contained, as illustrated in FIG. 8, for example, the load of the arithmetic processing related to the image analysis can be reduced as much as possible.

Figure 9:
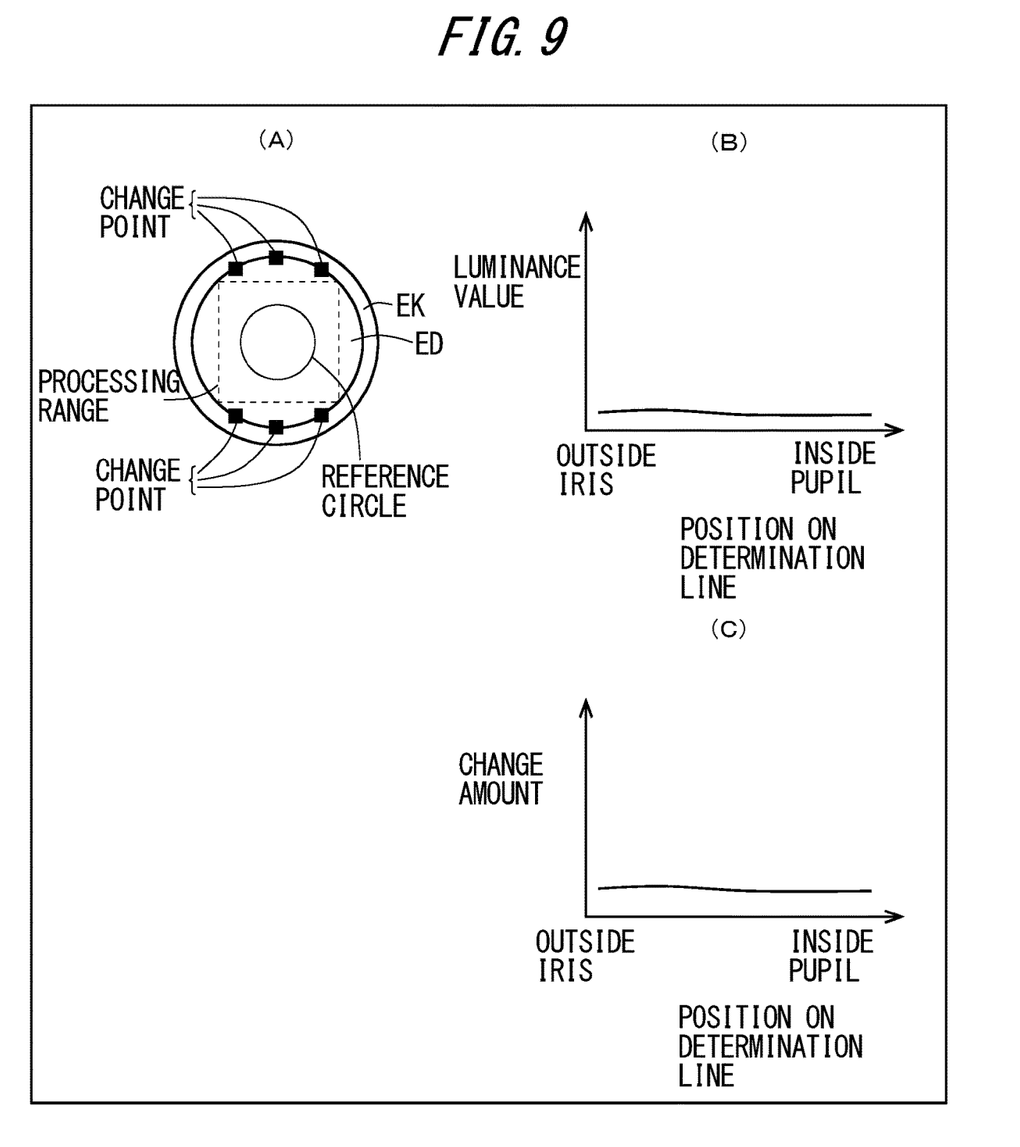
FIG. 9 is a diagram depicting an image of the content of the detection of the pupil diameter in the case where a range of the image to scan the luminous values is limited.

FIG. 9 is a diagram depicting an image of the content of the detection of the pupil diameter in the case where a range of the image, where the luminance values are scanned, is limited. In the case of limiting the range of the image where the luminance values are scanned, the "processing range", in which the boundary point extraction processing is performed, may be included within the range of the pupil ED. In such a case, if a luminance value of each pixel is scanned along the determination line HL, the luminance values may become low values without much change, as indicated in FIG. 9(B). Therefore the continuous data that is acquired by performing differentiation on the continuous data of these luminance values also become low values, which do not indicate any significant change, as indicated in FIG. 9(C). In the ophthalmic photographing apparatus 1, as described with reference to the flow chart in FIG. 3, it is determined in step S106 whether the luminous values of the pixels along the determination line HL are a predetermined numeric value or less, hence in the case where the "processing range" is included within the range of the pupil ED, it is determined that the luminance values of the pixels along the determination line HL are a predetermined numeric value or less, and the determination result in the processing in step S106 becomes Yes.

The color of the iris EK may be different depending on the subject. Examples of the color of the iris EK are brown and blue. The luminance of the illuminated iris EK differs depending on the color of the iris EK. Therefore in the ophthalmic photographing apparatus 1 of the above embodiment, when change points are extracted from the data acquired by differentiation performed on the continuous data of the luminance value of each pixel along the determination line HL, the color of the iris EK may be automatically determined based on the data on the change amount. For example, the value of the data at the change point, in the data acquired by performing differentiation on the continuous data of the luminance value of each pixel along the determination line HL, is greater in the case where the iris EK is brown than in the case where the iris EK is blue. Hence whether the subject eye E is brown or blue can be automatically determined by sorting the values of the data at the change points using a threshold. The determination result may be used for changing the light quantity of the illumination when the ocular fundus is observed or photographed, or may be used to verify the identity of the subject in a medical institution where many patients are examined.

REFERENCE SIGNS LIST

1 Ophthalmic photographing apparatus
2 Objective lens
2A Anterior ocular segment illumination
2B Anterior ocular segment imaging lens
3 Perforated mirror
4 Focus lens
5 Half mirror
6 Internal fixation lamp
7 Relay lens
8 Focus dot mirror
9 Focus index projection system
10 Black dot plate glass
11 Relay lens
12 Ring slit
13 Diffusion plate
14 Illumination for photographing
15 Illumination for observation
16 Imaging lens
17 Narrow angle lens
18 Wide angle lens
20 Image sensor
21 CPU board
22 LCD panel
23 LCD backlight
24 Operation unit
25 Main board
26 Electronic components
E Subject eye
ED Pupil
EK Iris
WDL, WDR Index
WGL, WGR Working alignment guide
HL Determination line

What is claimed is:

1. An ophthalmic photographing apparatus comprising:
an anterior ocular segment illumination unit for illuminating an anterior ocular segment of a subject eye with invisible light;
an imaging element that is sensitive to at least invisible light and that captures an image of the subject eye; and
a processor for processing the image captured by the imaging element, wherein
when an image of an index projected onto the anterior ocular segment satisfies a predetermined condition, the processor starts detection of a pupil diameter of the subject eye by using the image on the imaging element formed by reflected light from the anterior ocular segment, which is reflected light of invisible light emitted from the anterior ocular segment illumination unit,
wherein the processor scans luminance values along a virtual line within the image, the virtual line intersecting with at least a boundary between an iris and a pupil of the subject eye, and wherein the processor detects the pupil diameter from a position of a boundary point between the iris and the pupil of the subject eye extracted based on a change amount of the luminance values.

2. The ophthalmic photographing apparatus according to claim 1, wherein the processing unit, when detecting that an image of an index for distance measurement projected onto the anterior ocular segment is at a predetermined position within the image formed on the imaging element, starts detection of the pupil diameter by using the image on the imaging element formed by reflected light from the anterior ocular segment, which is reflected light of invisible light emitted from the anterior ocular segment illumination unit.

3. The ophthalmic photographing apparatus according to claim 1, wherein
the ophthalmic photographing apparatus further comprises switching unit for switching a region to be imaged on the imaging element between the ocular fundus of the subject eye and the anterior ocular segment, and
the processing unit, upon completion of the detection of the pupil diameter, uses the switching unit to switch the region to be imaged on the imaging element from the anterior ocular segment to the ocular fundus.

4. The ophthalmic photographing apparatus according to claim 1, wherein the processing unit scans the luminance values along a plurality of the virtual lines, and detects the pupil diameter from positions of a plurality of the boundary points.

* * * * *